(12) United States Patent
Hirahara et al.

(10) Patent No.: US 7,289,646 B2
(45) Date of Patent: Oct. 30, 2007

(54) METHOD AND SYSTEM FOR SIMULTANEOUSLY IMAGING MULTIPLE VIEWS OF A PLANT EMBRYO

(75) Inventors: Ed Hirahara, Federal Way, WA (US); Paul Spencer, Pullman, WA (US)

(73) Assignee: Weyerhaeuser Company, Federal Way, WA (US)

( * ) Notice: Subject to any disclaimer, the term of this patent is extended or adjusted under 35 U.S.C. 154(b) by 676 days.

(21) Appl. No.: 10/861,076

(22) Filed: Jun. 4, 2004

(65) Prior Publication Data

US 2004/0263957 A1 Dec. 30, 2004

(51) Int. Cl.
*G06K 9/00* (2006.01)
(52) U.S. Cl. ................ 382/110; 382/274; 47/57.7
(58) Field of Classification Search .......... 382/100, 382/107, 110, 168, 181, 190, 201, 203, 256, 382/274, 276, 291, 305, 318; 47/57.6; 406/3, 406/182; 800/260; 396/333
See application file for complete search history.

(56) References Cited

U.S. PATENT DOCUMENTS

| | | | |
|---|---|---|---|
| 3,515,475 A | 6/1970 | Zukor | |
| 4,213,684 A * | 7/1980 | Frosch et al. | ............... 396/333 |
| 4,309,094 A | 1/1982 | Bollen | |
| 5,659,623 A | 8/1997 | Conrad | |
| 5,687,504 A * | 11/1997 | Carlson et al. | ............. 47/57.6 |
| 5,917,926 A | 6/1999 | Leverett | |
| 6,014,451 A | 1/2000 | Berry et al. | |
| 6,122,045 A | 9/2000 | Pike et al. | |
| 6,354,770 B1 * | 3/2002 | McKinnis | ................... 406/182 |
| 6,684,564 B1 * | 2/2004 | Hirahara | .................... 47/57.6 |
| 6,709,203 B2 * | 3/2004 | McKinnis | ...................... 406/3 |
| 6,750,376 B1 * | 6/2004 | Carman | ...................... 800/260 |

FOREIGN PATENT DOCUMENTS

| | | |
|---|---|---|
| DE | 197 16 468 A1 | 10/1998 |
| WO | WO 99/20977 A1 | 4/1999 |
| WO | WO 99/63057 | * 12/1999 |
| WO | WO 00/33027 A1 | 6/2000 |

* cited by examiner

*Primary Examiner*—Seyed Azarian
(74) *Attorney, Agent, or Firm*—Christensen O'Connor Johnson Kindness

(57) ABSTRACT

The invention provides a method and system for simultaneously imaging multiple views of a plant embryo. First, the method provides a camera for receiving a first view of a plant embryo (e.g., the top view). Second, the method provides a first reflecting surface for receiving and reflecting a second view of the plant embryo (e.g., the side view) toward the camera. Thus, the method permits simultaneously imaging both the first and second views of the plant embryo. In one embodiment, the method further provides a second reflecting surface for receiving and reflecting a third view (e.g., the end view) of the plant embryo toward the camera, so that the camera can simultaneously image the first, second, and third views of the plant embryo. The invention reduces the time required to obtain multiple views of an embryo, which can then be analyzed to classify the embryos according to their germination vigor.

22 Claims, 5 Drawing Sheets

METHOD AND SYSTEM FOR SIMULTANEOUSLY IMAGING MULTIPLE VIEWS OF A PLANT EMBRYO

FIELD OF THE INVENTION

The invention is directed to imaging plant embryos for determination of suitability for germination or other treatment, and more particularly, to simultaneously imaging multiple views of a plant embryo so as to permit efficient mass selection of plant embryos suitable for incorporation into manufactured seeds.

BACKGROUND OF THE INVENTION

Reproduction of selected plant varieties by tissue culture has been a commercial success for many years. The technique has enabled mass production of genetically identical selected ornamental plants, agricultural plants and forest species. The woody plants in this last group have perhaps posed the greatest challenges. Some success with conifers was achieved in the 1970s using organogenesis techniques wherein a bud, or other organ, was placed on a culture medium where it was ultimately replicated many times. The newly generated buds were placed on a different medium that induced root development. From there, the buds having roots were planted in soil.

While conifer organogenesis was a breakthrough, costs were high due to the large amount of handling needed. There was also some concern about possible genetic modification. It was a decade later before somatic embryogenesis achieved a sufficient success rate so as to become the predominant approach to conifer tissue culture. With somatic embryogenesis, an explant, usually a seed or seed embryo, is placed on an initiation medium where it multiplies into a multitude of genetically identical immature embryos. These can be held in culture for long periods and multiplied to bulk up a particularly desirable clone. Ultimately, the immature embryos are placed on a development or maturation medium where they grow into somatic analogs of mature seed embryos. As used in the present description, a "somatic" embryo is a plant embryo developed by the laboratory culturing of totipotent plant cells or by induced cleavage polyembryogeny, as opposed to a zygotic embryo which is a plant embryo removed from a seed of the corresponding plant. These embryos are then individually selected and placed on a germination medium for further development. Alternatively, the embryos may be used in artificial seeds, known as manufactured seeds.

There is now a large body of general technical literature and a growing body of patent literature on embryogenesis of plants. Examples of procedures for conifer tissue culture are found in U.S. Pat. Nos. 5,036,007 and 5,236,841 to Gupta et al.; U.S. Pat. No. 5,183,757 to Roberts; U.S. Pat. No. 5,464,769 to Attree et al.; and U.S. Pat. No. 5,563,061 to Gupta. Further, some examples of manufactured seeds can be found in U.S. Pat. No. 5,701,699 to Carlson et al., the disclosure of which is hereby expressly incorporated by reference. Briefly, a typical manufactured seed is formed of a seed coat (or a capsule) fabricated from a variety of materials such as cellulosic materials, filled with a synthetic gametophyte (a germination medium), in which an embryo surrounded by a tube-like restraint is received. After the manufactured seed is planted in the soil, the embryo inside the seed coat develops roots and eventually sheds the restraint along with the seed coat during germination.

One of the more labor intensive and subjective steps in the embryogenesis procedure is the selection of individual embryos suitable for germination (e.g., incorporation into manufactured seeds). The embryos harvested from the maturation medium may be present in a number of stages of maturity and development. Those that are most likely to successfully germinate into normal plants are preferentially selected using a number of visually evaluated screening criteria. Morphological features such as axial symmetry, cotyledon development, surface texture, color, and others are examined and applied as a pass/fail test before the embryos are passed on for germination. This is a skilled yet tedious manual labor that is time consuming and expensive. Further, it poses a major production bottleneck when the ultimate desired output will be in the millions of plants.

It has been proposed to use some form of instrumental image analysis for embryo selection to replace the visual evaluation described above. For example, PCT application Ser. No. PCT/US00/40720 (WO 01/13702 A2) discloses an embryo delivery system for manufactured seeds including an imaging camera, which acquires and digitally stores images of embryos. The images are then sent to a computer, which classifies the embryos according to their desirability (i.e., likelihood to germinate and grow into normal plants) based on predetermined parameters (axial symmetry, cotyledon development, surface texture, color, etc.) using a classification method disclosed in PCT application Ser. No. PCT/US99/12128 (WO 99/63057). Referring to FIG. 1, to obtain sufficient information, typically three orthogonal views of an embryo 10 (typically of up to about 5 mm in length) are imaged using three separate cameras 11a, 11b, 11c, or moving a single camera into three separate positions. The three illustrated views are a top view, a side view, and an end view (viewing the cotyledon end 12 of the embryo 10 in FIG. 1). The disclosure of these two PCT applications is hereby expressly incorporated by reference.

While the instrumental imaging analysis could replace the costly manual labor required to classify embryos based on their desirability, mass classification of embryos, in particular for the purpose of mass production of manufactured seeds, would require further shortening of time and lessening of operation required to classify embryos. The present invention is directed to meeting this requirement.

SUMMARY OF THE INVENTION

The invention provides a method of simultaneously imaging multiple views of a plant embryo. First, the method provides a camera for receiving a first view of a plant embryo (e.g., the top view). Second, the method provides a first reflecting surface for receiving and reflecting a second view of the plant embryo (e.g., the side view) toward the camera. Thus, using the camera, the method permits simultaneously imaging both the first and second views of the plant embryo. In one embodiment, the method further provides a second reflecting surface for receiving and reflecting a third view (e.g., the end view) of the plant embryo toward the camera, so that the camera can simultaneously image the first, second, and third views of the plant embryo.

According to one aspect of the invention, the three views of a plant embryo are orthogonal to each other.

According to another aspect of the invention, the reflecting surfaces are provided in the form of reflecting prisms.

According to another aspect of the invention, the reflecting surfaces are provided in the form of mirrors.

According to yet another aspect of the invention, a light source is provided adjacent to the plant embryo to illuminate the plant embryo during image acquisition. Further, a cube-like enclosure, the interior surface of which is advantageously a white diffuse reflecting surface, may be provided to provide for diffuse lighting (substantially uniform illumination from all directions). The diffuse lighting arrangement eliminates shadows and prevents specular reflections from any wet or shiny areas on the surface of the embryo or from the interior surface of the enclosure. The enclosure also prevents undesirable light from reaching the image sensor of the camera. The enclosure including its various components is referred to as an "imaging cube."

The invention also offers a system for simultaneously imaging multiple views of a plant embryo, including generally three elements: a camera for receiving a first view of a plant embryo; a first reflecting surface for receiving and reflecting a second view of the plant embryo toward the camera; and a second reflecting surface for receiving and reflecting a third view of the plant embryo toward the camera. In the system, the camera is used to simultaneously image the first, second, and third views of the plant embryo.

According to one aspect of the invention, the system of the present invention further includes a cube-like enclosure that is configured to substantially enclose the first and second reflecting surfaces and the embryo to be imaged, so as to provide diffuse lighting and to prevent undesirable light from reaching the image sensor of the camera. In one embodiment, the cube includes generally three openings: first opening to transmit the multiple views of the embryo to the camera; a second opening for receiving light from a light source to illuminate the plant embryo inside the cube during image acquisition; and a third opening for receiving the plant embryo to be viewed, perhaps as placed on an elevatable platform. In operation, the platform is lowered and a plant embryo to be viewed is placed thereon. Thereafter, the platform carrying the embryo is elevated to be received within the third opening of the cube, so as to substantially enclose the embryo to be imaged within the cube.

One preferred embodiment of the platform includes a dark non-specular non-reflective surface area so as to provide a dark background and hence the maximum contrast for the top view image of the embryo. Also preferably, similar dark vertical surfaces may be provided opposite the first and second reflecting surfaces, respectively, to provide dark backgrounds for the side view and the end view.

As will be apparent to those skilled in the art, the present invention offers several significant advantages over the previous method of taking images of an embryo using three orthogonally arranged cameras. First, there is no need to orient the embryo when taking one image relative to the orientation of the other two images, since three views of the embryo are taken simultaneously (with their relative orientation being fixed due to the fixed relationship of the camera and the reflecting surfaces). Second, the time required to send the three views of an embryo to a computer for analysis is cut by two thirds because, according to the invention, a single image combining all three views of an embryo can be transmitted to the computer. Thus, the present invention substantially shortens the time and operation required to obtain multiple views of an embryo, which can then be used to classify the embryos based on their desirability (or germination vigor).

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
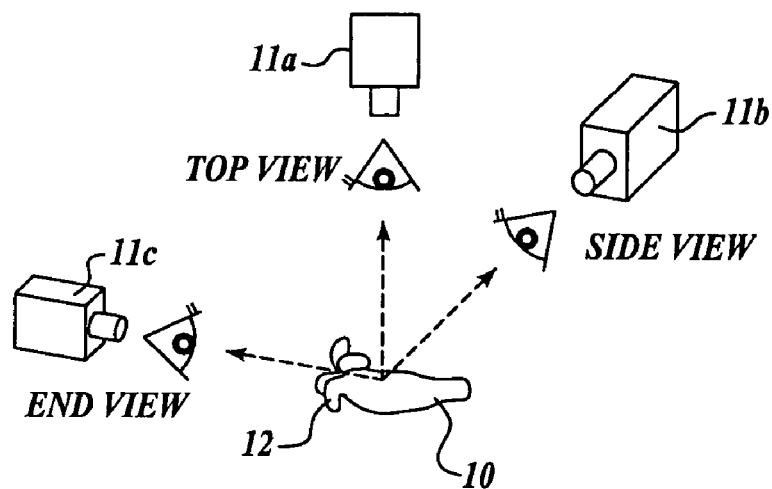
FIG. 1 illustrates a prior method of obtaining three orthogonal views of a plant embryo using three separate cameras that are arranged orthogonal to each other.
Figure 2:
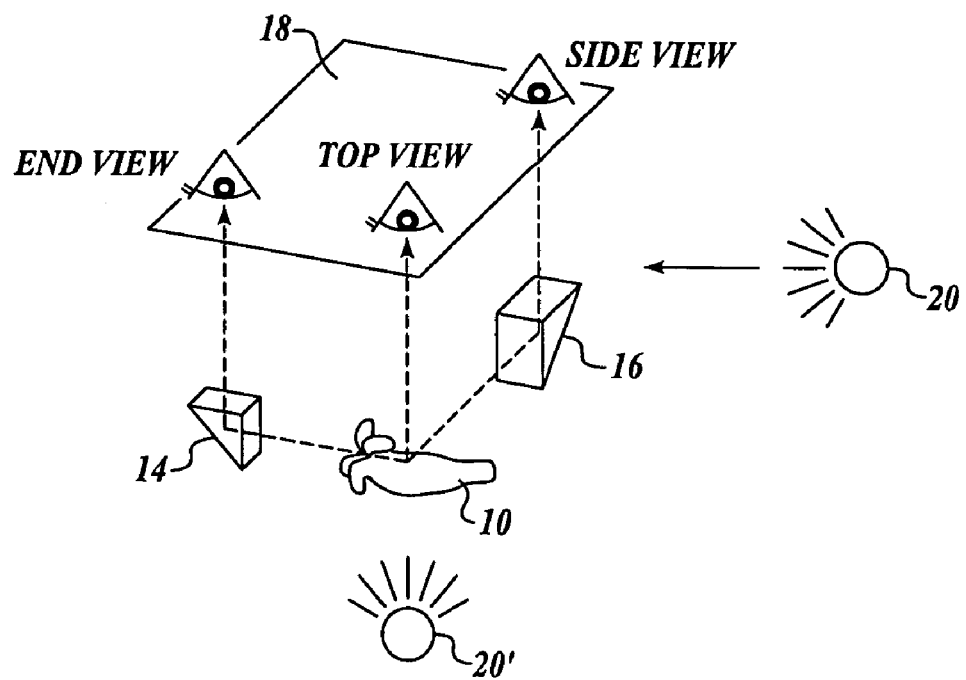
FIG. 2 illustrates a method of obtaining three orthogonal views of a plant embryo using a single camera, according to the present invention.

FIG. 2 schematically illustrates the method of the present invention for simultaneously imaging multiple views of a plant embryo. The method involves directly imaging a first view of a plant embryo 10 (the top view in FIG. 2) on an image plane 18 of a camera; and using a first reflecting surface 14 to receive and reflect a second view of the embryo (the cotyledon end view in FIG. 2) toward the image plane 18 of the same camera. Thus, an image combining both the first and second views (i.e., the top and end views in the illustrated embodiment) can be taken. In one embodiment, the method further involves using a second reflecting surface 16 to receive and reflect a third view of the embryo (the side view in FIG. 2) toward the image plane 18 of the same camera. According to this arrangement, a camera with the image plane 18 can simultaneously acquire the first view (e.g., the top view) directly from the embryo 10, the second view (e.g., the cotyledon end view) via the first reflecting surface 14, and the third view (e.g., the side view) via the second reflecting surface 16. In other words, a single image taken at the image plane 18 includes three different views of an embryo.

As in this example, the first, second, and third views may be orthogonal to each other, though the angular relationship of the three views is not limited to an orthogonal arrangement. Also, in the illustrated embodiment, both the first and second reflecting surfaces 14 and 16 are provided as reflecting prisms, though any other optical elements that provide reflecting surfaces may be used, such as reflecting mirrors. If necessary, a suitable light source 20 (or 20) may be arranged to illuminate the embryo 10 during image acquisition.

Figure 3A:
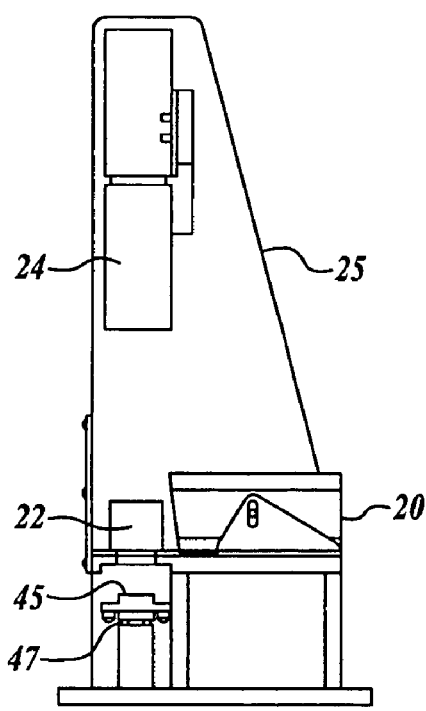
FIGS. 3A and 3B illustrate a system for simultaneously obtaining multiple views of a plant embryo according to the present invention, wherein, in FIG. 3A a platform is lowered to load an embryo to be imaged thereon, while in FIG. 3B the platform carrying the embryo is elevated into an imaging cube of the system.
Figure 4A:
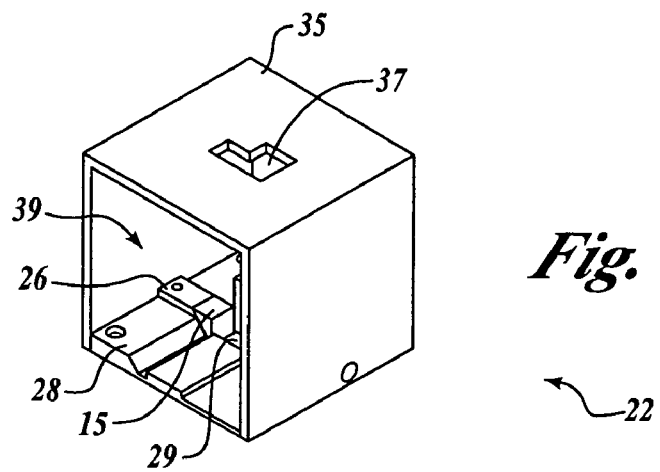
FIG. 4A is a perspective view of the imaging cube of the system of FIGS. 3A and 3B.
Figure 4B:
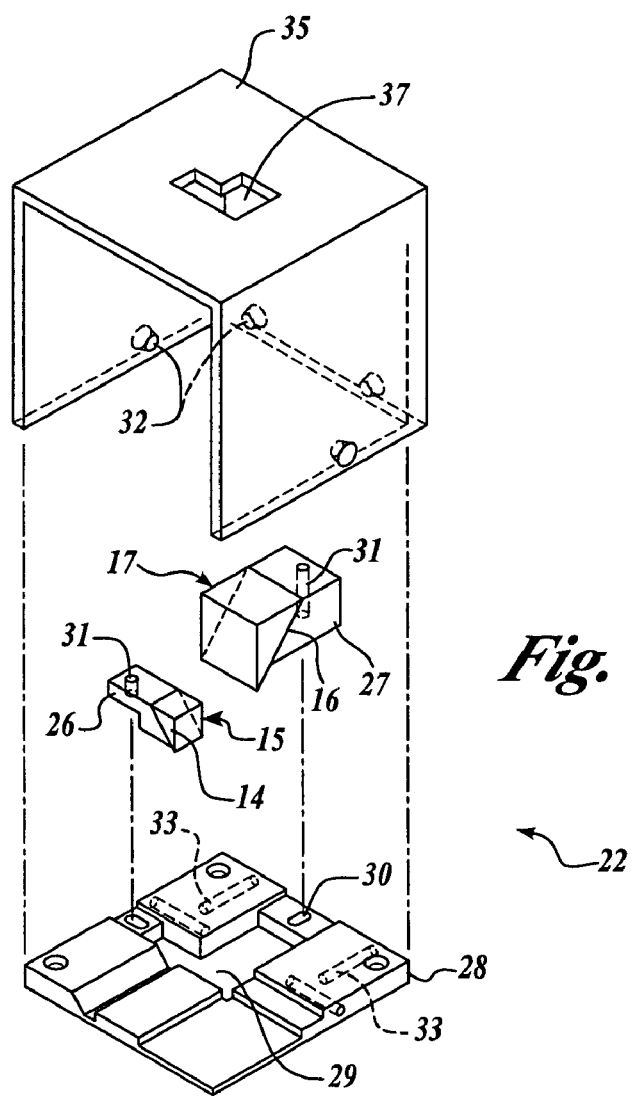
FIG. 4B is an exploded view of the same imaging cube.

Referring now to FIG. 3A, one embodiment of the proposed system is disclosed. The system includes an imaging cube 22, a light source 20, and a camera 24, arranged on a suitable stand structure 25. Any light source 20 suitable for illuminating the plant embryo to be imaged may be used. In some situations, for example where an ambient light is sufficient for illuminating the plant embryo to be imaged, a light source may not be required. Also, any suitable camera 24 may be used, preferably a digital camera containing a charge-coupled device (CCD) linked to a digital storage device, so as to permit subsequent digital analysis of the embryo image for classification purposes. Referring additionally to FIGS. 4A and 4B, in one embodiment, the imaging cube 22 includes two right-angle prisms 15 and 17, which provide the first and second reflecting surfaces 14 and 16, respectively. The prisms 15 and 17 are arranged on (e.g., adhered to) slanted blocks 26 and 27, respectively, which in turn are secured to a base plate 28 via suitable fasteners (not shown) extending through holes 30 and 31. The holes 30 and 31 may be threaded, when threaded fasteners are used. The base plate 28 defines a central opening 29 which, after the slanted blocks 26 and 27 and the prisms 15 and 17 are secured to the base plate 28, provides a generally rectangular-shaped opening (see FIG. 4A) for receiving a rectangular-shaped platform (or tray) carrying a plant embryo to be imaged, as will be more fully described below. A cube 35 including suitably arranged holes 32 are placed over the base plate 28, and fasteners (not shown) are placed extending through the holes 30 and holes 33 provided in the base plate 28 to complete the imaging cube 22. The cube 35 includes a camera viewing hole 37. As shown in FIG. 4A, the imaging cube 22 is enclosed except for one open surface 39, which is to face the light source 20 for receiving embryo illuminating light. (See FIG. 3A.) Alternatively, the surface 39 may be formed at least partially with a diffusing light transmissive material, such as ground glass, through which light from the light source 20 is received.

In one preferred embodiment, the interior surface of the cube 35 is formed as a white diffuse reflecting surface to provide diffuse lighting. Diffuse lighting (substantially uniform illumination from all directions) eliminates shadows and bright spots due to specular reflections from wet or shiny areas on the embryo surface or from the interior surface of the cube 35. Thus, diffuse lighting makes the resulting embryo image substantially free of shadows and specular reflections and therefore simpler to analyze.

The base plate 28 and the cube 35 may be formed of any suitable material, such as injection molded plastic. It should be understood that FIGS. 4A and 4B illustrate merely one embodiment of the imaging cube 22, and various other configurations of the imaging cube 22 (not limited to the illustrated cube shape) are possible. The particular shape and method of assembling each component/element of the imaging cube 22 (e.g., the locations of fasteners) may vary according to each application, as will be apparent to those skilled in the art. In particular, the reflecting surfaces 14 and 16 may be provided by any suitable optical elements, as described above, and if provided in the form of reflecting prisms, may be provided by various prisms including roof prisms, dove prisms, pentagon prisms, etc., not limited to the illustrated right-angle prisms.

Figure 5:
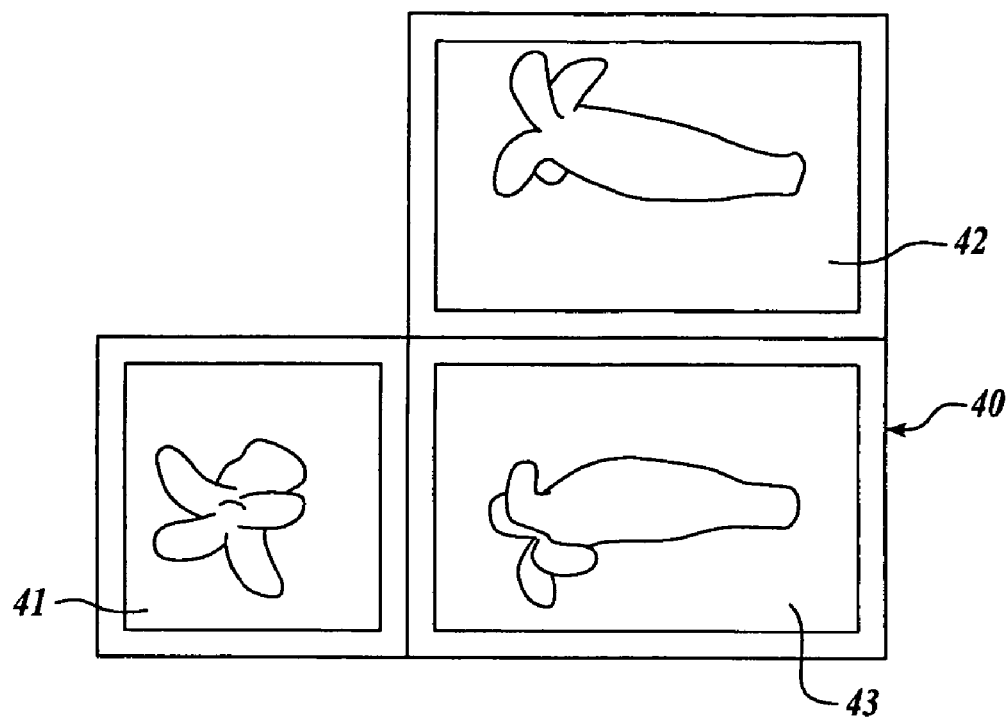
FIG. 5 is a sample schematic image of an embryo, including three orthogonal views of the embryo that are taken simultaneously.

The camera viewing hole 37, provided on the illustrated top surface of the imaging cube 22, is for the camera 24 to view an embryo placed inside the imaging cube 22. (See FIG. 3A for the relative positioning of the imaging cube 22 and the camera 24.) Referring additionally to FIG. 5, a sample image 40 taken by the camera 24 includes three views of an embryo: an end view 41 received and reflected by the first reflecting surface 14 (or the first prism 15) toward the camera 24; a side view 42 received and reflected by the second reflecting surface 16 (or the second prism 17) toward the camera 24; and a top view 43 received directly by the camera 24. In the illustrated embodiment, the camera viewing hole 37 is generally L-shaped to correspond with the shape of the image 40 combining three orthogonal views of an embryo taken simultaneously, although the shape of the viewing hole 37 is not limited to this particular configuration. In the illustrated embodiment, the cube 35 with the camera viewing hole 37 and the base plate 28 are provided and configured so as to acquire three views of an embryo while providing diffuse illumination for the embryo. However, such an arrangement may not be necessary depending on a particular application. The cube 35 and the base plate 28 also generally serve to protect the reflecting surfaces 14 and 16 from external elements that could damage or misalign the reflecting surfaces.

Figure 3B:
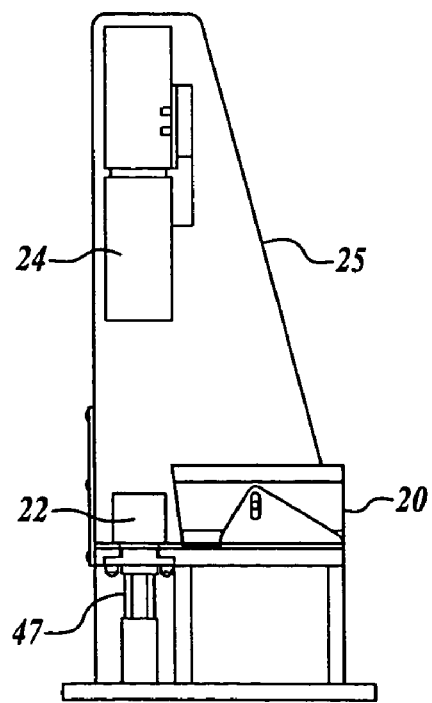
Figure 6:
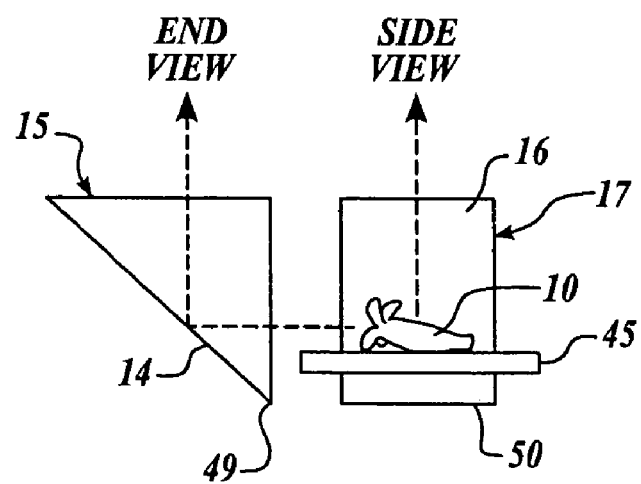
FIG. 6 schematically illustrates the positioning of a plant embryo to be imaged relative to two reflecting surfaces.

Referring to FIGS. 3A and 6, in one embodiment, an embryo 10 to be imaged is placed on a generally rectangular platform 45 coupled to an elevator actuator 47. The elevator actuator 47 may be driven and controlled by any suitable means, such as by an electric or hydraulic motor. Initially, the platform is lowered by the elevator actuator 47 relative to the imaging cube 22, and the embryo 10 to be imaged is placed on the platform 45. Thereafter, referring to FIG. 3B, the elevator actuator 47 raises the platform 45 carrying the embryo 10 until the platform 45 is generally received within the central opening 29 of the base plate 28 of the imaging cube 22. In this configuration, after the platform 45 carrying the embryo 10 is raised and received by the central opening 29 having a shape corresponding to the shape of the platform 45, the embryo 10 is substantially enclosed within the imaging cube 22, except for the cube's open surface 39 facing the light source 20 and the camera viewing hole 37 for transmitting the embryo image to the camera 24. Thus, this embodiment is advantageous in preventing any undesirable light not originating from the embryo 10 from reaching the camera 24. To this end, the imaging cube 22, including the cube 35, the base plate 28, and the platform 45, may be formed of generally opaque material that blocks ambient light.

Figure 7:
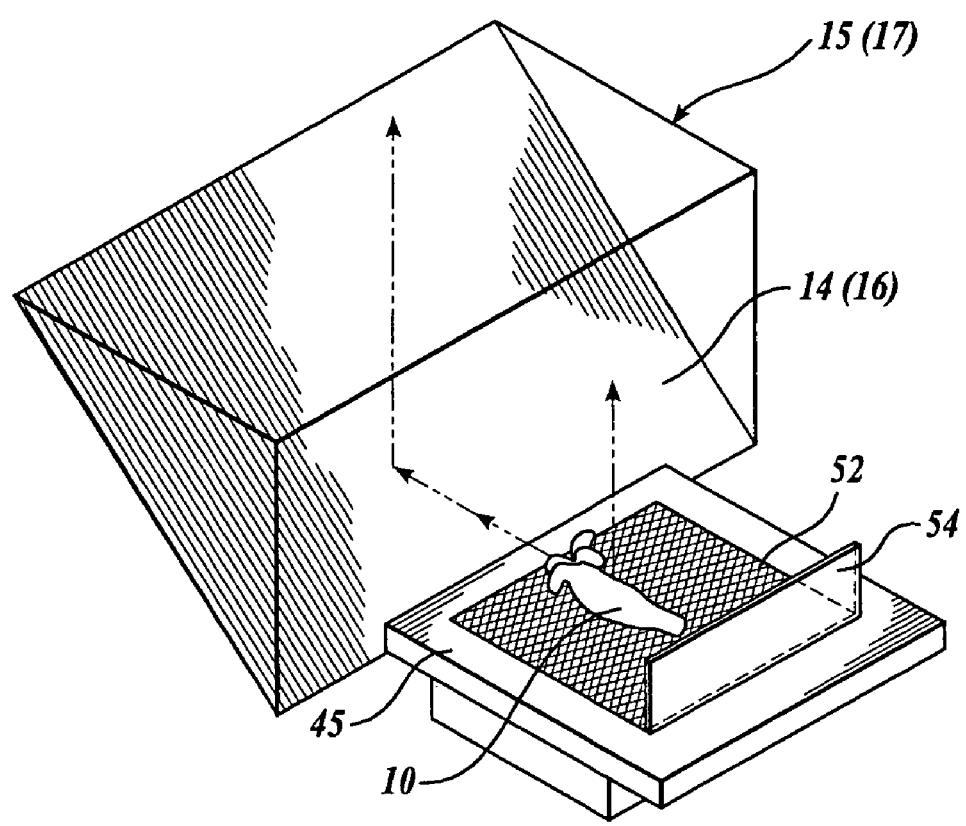
FIG. 7 schematically illustrates arranging dark backgrounds for a plant embryo to provide the maximum contrast for the embryo image.

As specifically illustrated in FIG. 6, preferably the platform 45 is configured to be raised above the lower edge portions 49 and 50 of the reflecting surfaces 14 and 16 so that a complete view of the embryo 10 can be received and reflected by the flecting surfaces 14 and 16 without distortion. Further preferably, the edge portions 49 and 50 of the reflecting surfaces (the prisms in the illustrated embodiment) are rounded so as to permit obtaining a flat view of an embryo without any clipping. Still further, referring to FIG. 7, in one preferred embodiment, the platform 45 includes a dark non-specular and non-reflective surface area 52 to provide the maximum contrast for the top view image of the embryo 10. Likewise, similarly dark and generally vertical background surfaces 54 may be provided, generally opposite the first and second reflecting surfaces 14 and 16 across the embryo 10, to provide the maximum contrast for the second and third views (e.g., the side view and the end view) of the embryo image. In FIG. 7, only one vertical background surface 54 is shown to provide a dark background for the "end view" of the embryo 10.

The means for positioning an embryo for imaging is not limited to the combination of the platform 45 and the elevator actuator 47 described above. For example, an embryo to be imaged may be placed on a horizontally movable platform, or a two- or three-dimensionally movable platform, to be positioned relative to the camera 24 generally between the two reflecting surfaces 14 and 16. Alternatively, an embryo may be positioned for imaging using a mini-robotic pick and place systems, a suction-based pick and place systems (e.g., pipettes), or even manually. It should be understood that the present invention is not limited to any particular means for positioning a plant embryo for imaging.

It should also be understood that the present invention is not limited to the particular embodiment discussed hereinabove for taking the end view and the side view of an embryo via two reflecting surfaces. For example, two reflecting surfaces may be used to take the top view and the side view, or the top view and the end view, of an embryo, while the third view is taken directly by the camera. Depending on which view is to be taken directly by the camera, the relative placement of the camera 24 with respect to the imaging cube 22 may vary, and is not limited to the particular arrangement illustrated in FIG. 3A. For example, the camera 24 may be placed generally horizontally adjacent to the imaging cube 22 so as to directly image either the end view or the side view of an embryo. Further alternatively, the arrangement of the light source 20 relative to the imaging cube 22 is not limited to the arrangement illustrated in FIG. 3A. For example, the light source 20 may be provided generally beneath the imaging cube 22 (as in the light source 20' in FIG. 2), though in such a case the bottom surface of the imaging cube 22 facing the light source 20 must be configured to permit transmission of the illuminating light. As a further example, in addition to the two reflecting surfaces 14 and 16, further reflecting surfaces may be used to simultaneously image two opposite side views (the right side view and the left side view) and/or two opposite end views (the cotyledon end view and the radicle end view) of an embryo. For example, if two side views and two end views, as well as the top view, are to be imaged simultaneously, two additional reflecting surfaces arranged generally opposite the first and second reflecting surfaces 14 and 16, respectively, will be used.

It should be understood that the present method and system for simultaneously imaging multiple views of an embryo can be applied in obtaining multiple sets of spectral data from an embryo regarding absorption, transmittance, or reflectance of electromagnetic radiation (not limited to visible light) by the embryo. For example, classification of embryos based on the analysis of spectral data collected from the embryos using IR spectroscopy was disclosed in PCT application Ser. No. PCT/US99/12128 (WO 99/63057), discussed above. Spectroscopic analysis, including IR spectroscopy, NIR spectroscopy, and Raman spectroscopy, permits identification of chemical composition (surface chemistry) of an embryo. It is known that the embryo quality is related to gross chemical composition of the embryo or its parts, for example the amounts of water and storage compounds (proteins, lipids, carbohydrates, etc.). Therefore, spectroscopic analysis may be used to classify embryos according to their desirability. Accordingly, as used in the present description, obtaining an image or imaging is not limited to obtaining a visible image of an embryo, and may include acquiring spectral data from an embryo (or its parts) to identify its chemical composition.

In one embodiment, the system of the present invention including the camera 24 and the imaging cube 22 may be incorporated into an automated manufactured seed delivery/manufacturing line, as disclosed in PCT application Ser. No. PCT/US00/40720 (WO 01/13702 A2), discussed above. For example, the elevatable platform 45 may be incorporated along a conveyor belt for delivering embryos, so that an embryo, upon being placed on the platform, can be elevated into the imaging cube 22 for imaging and subsequent analysis. Alternatively, the imaging cube 22 may be arranged to be lowered to the conveyor belt for imaging an embryo carried on the conveyor.

As will be apparent to those skilled in the art, the present invention offers several significant advantages over the previous method of taking multiple images of an embryo to obtain multiple views of the embryo, using multiple cameras (or multiple positioning of a camera). First, there is no need to orient the embryo when taking one image relative to the orientation of the other image(s), since multiple views of the embryo are taken simultaneously, with their relative orientation being fixed due to the fixed relationship of the camera and the reflecting surface(s). Second, the time required to send the multiple views of an embryo to a computer for analysis is substantially reduced because, according to the present invention, a single image combining multiple views of an embryo can be transmitted to the computer at once. Thus, the present invention significantly shortens the time required to obtain multiple views of an embryo, which can then be used to classify the embryos based on their desirability (or germination vigor). Accordingly, the present invention is useful in mass selection of desirable embryos suitable for incorporation into manufactured seeds, and hence in mass production of manufactured seeds.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A method of simultaneously imaging multiple views of a plant embryo, comprising:
    substantially enclosing the embryo to be imaged so as to provide diffuse lighting for the embryo;
    providing a dark background for the embryo to be imaged so as to achieve the maximum contrast for an image of the embryo;
    providing a camera for receiving a first direct view of a plant embryo;
    providing a first reflecting surface for receiving and reflecting a second view of the plant embryo toward the camera; and
    using the camera, simultaneously imaging the first and second views of the plant embryo.

2. The method of claim 1, further comprising providing a second reflecting surface for receiving and reflecting a third view of the plant embryo toward the camera, wherein the camera is used to simultaneously image the first, second, and third views of the plant embryo.

3. The method of claim 2, wherein at least two of the first, second, and third views are orthogonal to each other.

4. The method of claim 2, wherein the first and second reflecting surfaces comprise reflecting prisms.

5. The method of claim 2, further comprising providing a third reflecting surface for receiving and reflecting a fourth view of the plant embryo toward the camera, wherein the fourth view comprises a view of the embryo that is generally opposite to the second or third view of the embryo, and the camera is used to simultaneously image the first, second, third, and fourth views of the plant embryo.

6. The method of claim 1, wherein the camera comprises a digital camera.

7. The method of claim 1, wherein the plant embryo comprises a somatic embryo.

8. The method of claim 1, further comprising providing a light source adjacent to the plant embryo to illuminate the plant embryo during image acquisition.

9. A system of simultaneously imaging multiple views of a plant embryo, comprising:
    an enclosure defining a camera viewing hole for transmitting an image of the embryo, a surface for receiving light from a light source, and an opening for receiving the plant embryo to be imaged, wherein the surface for receiving light from the light source comprises a surface at least partially formed of a diffusing light transmissive material;

a camera positioned relative to the enclosure for receiving a first direct view of a plant embryo;

a first reflecting surface for receiving and reflecting a second view of the plant embryo toward the camera; and a second reflecting surface for receiving and reflecting a third view of the plant embryo toward the camera;

wherein the camera is used to simultaneously image the first, second, and third views of the plant embryo.

10. The system of claim 9, wherein at least two of the first, second, and third views of the embryo are orthogonal to each other.

11. The system of claim 9, wherein the first and second reflecting surfaces comprise reflecting prisms.

12. The system of claim 11, wherein the first and second reflecting surfaces comprise right-angle prisms.

13. The system of claim 9, wherein the first and second reflecting surfaces comprise mirrors.

14. The system of claim 9, wherein the camera comprises a digital camera.

15. The system of claim 9, wherein the plant embryo comprises a somatic embryo.

16. The system of claim 9, wherein the plant embryo comprises a conifer embryo.

17. The system of claim 9, further comprising:

a third reflecting surface for receiving and reflecting a fourth view of the plant embryo toward the camera, the fourth view being generally opposite to the second view; and a fourth reflecting surface for receiving and reflecting a fifth view of the plant embryo toward the camera, the fifth view being generally opposite to the third view;

wherein the camera is used to simultaneously image the first, second, third, fourth, and fifth views of the plant embryo.

18. The system of claim 9, wherein the interior surface of the enclosure comprises a white diffuse reflecting material so as to provide substantially uniform lighting in all directions and prevent undesirable light from reaching an image sensor of the camera.

19. The system of claim 18, further comprising a light source provided adjacent to the enclosure for illuminating the plant embryo during image acquisition.

20. The system of claim 9, further comprising a movable platform for carrying a plant embryo thereon, the platform being moved between a first position at which a plant embryo is placed on the platform and a second position at which the platform carrying the embryo is received within the opening of the enclosure.

21. The system of claim 20, wherein the platform comprises a dark surface area to provide a background for the first view of the embryo.

22. The system of claim 21, further comprising a background surface arranged generally perpendicularly to the dark surface area of the platform to provide a background for the second or third view of the embryo.

* * * * *